Figure 1A:

United States Patent [19]

Thorns

[11] Patent Number: 5,510,241
[45] Date of Patent: Apr. 23, 1996

[54] **METHOD OF TESTING FOR THE PRESENCE OF SALMONELLA SEROTYPES EXPRESSING *SALMONELLA ENTERITIDIS* FIMBRIAL ANTIGEN (SEFA) AND REAGENTS THEREFORE**

[75] Inventor: Christopher J. Thorns, Woking, England

[73] Assignee: The Minister of Agriculture, Fisheries and Food in her Britannic Majesty's Government of the U.K. of Gt. Britain & N. Ireland, London, England

[21] Appl. No.: 449,922

[22] Filed: May 25, 1995

Related U.S. Application Data

[63] Continuation of Ser. No. 30,208, Mar. 26, 1993, abandoned.

[30] Foreign Application Priority Data

| Oct. 1, 1990 | [GB] | United Kingdom | 9021290 |
| Oct. 17, 1990 | [GB] | United Kingdom | 9022570 |
| Mar. 27, 1991 | [GB] | United Kingdom | 9106546 |

[51] Int. Cl.$^6$ ............ G01N 33/53; C07K 14/255; C07K 16/00
[52] U.S. Cl. ............ 435/7.3; 435/7.35; 435/240.27; 530/350; 530/387.1; 530/388.4; 530/389.5; 530/391.1; 530/391.3
[58] Field of Search ............ 435/7.35, 7.3, 435/7.32, 7.92, 240.27; 530/350, 387.1, 388.4, 389.5, 391.1, 391.3, 810, 811, 812

[56] References Cited

FOREIGN PATENT DOCUMENTS 8601805 3/1986 WIPO.

OTHER PUBLICATIONS

Manual of Clinical Microbiology, 4th Ed. Lennette edition (American Society for Microbiology, Washington DC) 1985, p. 1062.

American Type Culture Collection Catalogue of Bacteria and Phages, 17th Ed., 1989, pp. 295, 317, 342.

Handbook of Microbiological Media: Atlas et al, (CRC Press, Boca Raton) 1993, pp. 459, 801.

Feutrier et al, "Purification and Characteristics of Fimbriae from *Salmonella enteridites*", J. Bacteriol., 168(1): 221–227 (Oct. 1986).

Feutier et al, "Cloning and Expression of a *Salmonella enteriditis* Fimbrin Gene in *Escherichia coli*", J. Bacteriol., 170(9): 4216–4222 (Sep. 1988).

Thorns et al, "Detection of a Novel Fimbrial Structure on the Surface of *Salmonella enteriditis* by Using a Monoclonal Antibody", J. Clin. Microbiol., 28(11): 2409–2414 (Nov. 1990).

*Primary Examiner*—Toni R. Scheiner
*Assistant Examiner*—Patricia A. Duffy
*Attorney, Agent, or Firm*—Nixon & Vanderhye

[57] ABSTRACT

A method of testing for the presence of Salmonella serotypes *S. enteritidis* and *S. dublin* is provided. Novel monoclonal antibodies are used to detect the presence of an epitope specific for these serotypes in cultures which have been grown on selected media which enhance the expression of said epitope in fimbrial sites. Test kits utilizing the antigen or its epitopic parts, antibodies and/or the media are further provided.

31 Claims, 2 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 176 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Salmonella enteritidis/Salmonella dublin ( x i ) SEQUENCE DESCRIPTION: SEQ ID NO:1:

```
Met Leu Ile Val Asp Phe Trp Arg Phe Cys Asn Met Arg Lys Ser Ala
 1               5                   10                  15

Ser Ala Val Ala Val Leu Ala Leu Ile Ala Cys Gly Ser Ala His Ala
                20                  25                  30

Ala Gly Phe Val Gly Asn Lys Ala Glu Val Gln Ala Ala Val Thr Ile
            35                  40                  45

Ala Ala Gln Asn Thr Thr Ser Ala Asn Trp Ser Gln Asp Pro Gly Phe
        50                  55                  60

Thr Gly Pro Ala Val Ala Ala Gly Gln Lys Val Gly Thr Leu Ser Ile
65                  70                  75                  80
```

| | | | | | | | | | | | | | | | |
|---|---|---|---|---|---|---|---|---|---|---|---|---|---|---|---|
| Thr | Ala | Thr | Gly | Pro | His | Asn | Ser | Val | Ser | Ile | Ala | Gly | Lys | Gly | Ala |
| | | | | 85 | | | | | 90 | | | | | 95 | |
| Ser | Val | Ser | Gly | Gly | Val | Ala | Thr | Val | Pro | Phe | Val | Asp | Gly | Gln | Gly |
| | | | 100 | | | | | 105 | | | | | 110 | | |
| Gln | Pro | Val | Phe | Arg | Gly | Arg | Ile | Gln | Gly | Ala | Asn | Ile | Asn | Asp | Gln |
| | | 115 | | | | | 120 | | | | | 125 | | | |
| Ala | Asn | Thr | Gly | Ile | Asp | Gly | Leu | Ala | Gly | Trp | Arg | Val | Ala | Ser | Ser |
| | 130 | | | | | 135 | | | | | 140 | | | | |
| Gln | Glu | Thr | Leu | Asn | Val | Pro | Val | Thr | Thr | Phe | Gly | Lys | Ser | Thr | Leu |
| 145 | | | | | 150 | | | | | 155 | | | | | 160 |
| Pro | Ala | Gly | Thr | Phe | Thr | Ala | Thr | Phe | Tyr | Val | Gln | Gln | Tyr | Gln | Asn |
| | | | | 165 | | | | | 170 | | | | | 175 | |

METHOD OF TESTING FOR THE PRESENCE OF SALMONELLA SEROTYPES EXPRESSING *SALMONELLA ENTERITIDIS* FIMBRIAL ANTIGEN (SEFA) AND REAGENTS THEREFORE

This is a Rule 60 File Wrapper Continuation of application Ser. No. 08/030,208, filed Mar. 26, 1993, now abandoned.

This invention relates to a method of testing for micro-organisms of certain serotypes of the genus Salmonella, to antigens containing antigenic amino acid sequences expressed specifically by these serotypes, to specific monoclonal antibodies for use in said method and to kits for performing tests according to said method. The invention further provides hybridoma cells capable of producing the antibodies of the invention.

Organisms of the genus Salmonella, in particular *S. enteritidis. S. dublin* and *S. typhimurium,* are responsible for infective food poisoning caused by their ingestion in contaminated food. Infection with Salmonella may also occur as a result of contact with contaminated materials. Once ingested, Salmonella is able to establish itself in the gut and multiply rapidly, resulting in the appearance of clinical symptoms several days after the initial ingestion.

It is therefore highly desirable to provide test methods by means of which Salmonella organisms may be detected. In recent years immunological tests have been devised in which specific antibodies, particularly monoclonal antibodies ("MABs"), to specific antigens are raised and which, by exploiting the antigen-antibody specific binding reaction, the presence of the antigen can be detected. Such tests are fast and very specific.

It is known that Salmonella organisms have fimbria-like structures on their surface ( Duguid; J. P.; and R. R. Gillies. (1958) J. Pathol. Bacteriol. 75:519–520., and published evidence ( Clegg, S., and G. A. Gerlach (1987) J. Bacteriol. 169:934–938), suggests that there are antigenically distinct types of such fimbriae, ie possessing specific epitopes on the fimbrial antigens. The possibility of immunogenic tests for Salmonella, at least *S. enteritidis,* based upon these fimbrial antigens has been suggested (MAFF, Central veterinary Laboratory "Animal Health" (1989):33). Methods of raising MABs to antigens on the surface of microorganisms such as Salmonella are generally known.

Unfortunately known methods of raising antibodies to Salmonella surface antigens only go part way toward providing an immunological test for Salmonella. The basis of all such tests is to isolate microorganisms from a sample suspected of harbouring Salmonella organisms, then to grow the micro-organisms in vitro in a suitable culture medium until a quantity of the Salmonella sufficient to detect by such a test is believed to be present in the medium, and then applying the test. A problem occurs in that it is found that although Salmonella micro-organisms produce their fimbrial antigen when they grow in vivo, e.g. in the gut, in animal tissues or fluids, in food products and in some natural environments, many of the fimbrial antigens are not produced when they are grown in vitro on most culture media.

The inventors have investigated a range of culture media with the object of identifying the conditions necessary to induce the Salmonella micro-organisms *S. enteritidis* and *S. dublin* to produce a specific fimbrial antigen during in vitro culture so that immunological tests may be applied. This has provided the novel test method of this invention and also novel MABs designated herein as "MAB 69/25" and "MAB 71/3", produced by novel hybridoma cell lines, for use in the method. Samples of these cell lines have been deposited, on 11 Oct. and 19 Dec. 1990 respectively, at the European Collection of Animal cell Cultures, PHLS Centre for Applied Microbiology & Research, Porton Down, Salisbury, Wiltshire-SP4 OJG, United Kingdom and bear Accession numbers 90101101 and 90121902 respectively.

This investigation has provided a method for testing for the presence of micro-organisms of the species Salmonella, serotypes *S. enteritidis* and *S, dublin,* using the specific fimbrial antigen or an epitopic part thereof to bind them. Thus suspect biological fluids may be tested for such antibodies with the aim of identifying cases of *S. enteritidis* or *S. dublin* infection. The particular specific antigen identified by the present inventors has been found to be expressed almost exclusively by organisms of these two serotypes, the only other serotypes expressing it being considered very rare. A particular advantage of the method is thus that, out of the hundreds of serotypes of Salmonella found in nature, it can detect two of the most significant with regard to food poisoning.

This method is suitable for testing for the presence of Salmonella micro-organisms which have grown in vivo for example as found in clinical samples such as animal remains or products, food samples and infected environmental samples.

The inventors have found that exploitation of the ability of certain media to enable or cause Salmonella to produce this specific fimbrial antigen (Salmonella enteriditis fimbrial antigen-SEFA) during in vitro culture, whereby prior to the step of exposure to the antibody the micro-organisms are grown in vitro in or on such a medium such that they produce antigenic fimbriae having epitopic sites thereupon, allows reliable immuno-testing.

The influence of the medium appears to be particularly pronounced in the case of the said important Salmonella micro-organisms *S. enteritidis* and *S. dublin.* The method of the invention is therefore particularly suitable for the specific testing for the presence of *S. enteritidis* and *S. dublin* by the use of antibody-antigen binding, as these two Salmonella strains produce strongly antigenic fimbriae under the conditions of this invention, particularly of the preferred embodiment. The method appears to be applicable to testing for Salmonella in all types of samples, including food samples, environmental samples such as contaminated water, animal waste products, effluent etc.

The content of the culture medium is a crucial factor in the production of epitopic sites on the Salmonella fimbria. Media which are "defined" or at least "semi-defined" as understood in the art are preferred, for example media having at least 20% by weight of their nutrient composition made up of "defined" nutrients which are inorganic salts and/or organic compounds of known molecular structure. Peptone water and Enriched E broth (see Francis et al (1982) J. Clinical. Microbiol.. 15: 181–183) are examples of preferred liquid media although Slanetz broth, Heart infusion broth and Vogel Bonner broth are media capable of supporting expression of the specific sites by the target Salmonella organisms in many cases. Solid media examples include desoxycholate citrate agar, McConkey agar, Nutrient agar, Salmonella Shigella agar, Sheep blood agar, Xylose Lysine descholate. For more reliable and/or sensitive testing it may be necessary to use a medium that is mope potent in supporting the expression, as is evidenced by the experiments referred to herein; examples of such media being Oxoid Isosensitest and Sensitest agars.

Thus the present invention provides a method of testing for the presence of microorganisms of Salmonella serotypes *S. enteritidis* or *S. dublin* comprising exposing an analyte suspected of containing them or their fimbrial antigen (SEFA as described herein) to an antibody raised to said fimbrial antigen or to an epitopic part thereof, and then relating the occurrence of antibody-antigen specific binding to the presence of said serotypes.

The present invention further provides a method of testing for the presence of antibodies to SEFA comprising exposing SEFA (as described herein) or an epitopic part thereof to an analyte suspected of containing such antibodies and then relating the occurrence of antibody-antigen specific binding to the presence of said antibodies.

The present invention further provides a method of determining the identity of a Salmonella serotype as being either *S. enteritidis* or *S. dublin* comprising (a) exposing an analyte suspected of comprising at least one of said serotypes or their fimbrial antigen (SEFA as described herein) to an antibody raised to said fimbrial antigen, or a part thereof, and then relating the occurence of antibody-antigen specific binding to the presence of one of said serotypes then, (b) exposing a further sample of said analyte suspected of comprising at least one of said serotypes to an antibody raised to specifically bind to a first one of said serotypes but not the second and relating the occurence of antibody-antigen specific binding to the presence of that serotype and, optionally, (c) exposing a further sample of said analyte suspected of comprising at least one of said serotypes to an antibody raised to specifically bind to the second one of said serotypes but not to the first and relating the occurence of antibody-antigen specific binding to the presence of said second serotype.

The present invention further provides a method of testing for the presence of organisms of Salmonella serotypes *S. enteritidis* or *S. dublin* comprising (a) seeding a sample of an analyte suspected of containing them into/onto a culture medium selected for its ability to support expression of Salmonella enteritidis fimbrial antigen (SEFA); (b) culturing said seeded culture medium and; (c) exposing a sample derived from the culture derived from step (b) to an antibody raised to said fimbrial antigen, or an epitopic part thereof, and then relating the occurrence of antibody-antigen specific binding to the presence of said serotypes.

Conveniently the culture medium is one which has been selected by screening candidate culture media for the ability to support the expression of SEFA by *S. enteridiis* or a SEFA producing strain of *S. dublin*. The SEFA may be identified by comparison with previously isolated SEFA or by its ability to produce antibody-antigen specific binding with antibodies raised to SEFA or an epitopic part of SEFA. Particularly conveniently the expressed SEFA is identified using one of the monoclonal antibodies MAB 69/25 or MAB 71/3, from cells deposited as detailed above.

Particular SEFA expression supporting culture media identified by the inventors are Enriched E broth, Heart Infusion broth, peptone water pH 7.2, peptone water pH 6.0, Slanetz broth, desoxycholate citrate agar, McConkey agar, nutrient agar, Salmonella Shigella agar, Sheep blood agar, Xylose Lysine descholate, Medium A (as herein described), Sensitest agar, or Isosensitest agar.

Preferably the culture medium consists of Enriched E broth, peptone water pH 7.2, peptone water pH 6.0, Sensitest agar or Isosensitest agar; most preferably Sensitest agar or Isosensitest agar.

The present invention further provides hybidoma cells deposited at the ECACC, Porton Down under Accession numbers 90101101 and 90121902 as described above which are capable of producing MABs 69/25 and 71/3 by use of general techniques known in the art, and provides those antibodies themselves and methods of identifying SEFA Using them.

The present invention further provides kits for performing the methods of the invention comprising (a) cells which are capable of producing antibodies which are capable of specifically binding to SEFA or an epitopic part thereof, and/or (b) the antibodies themselves. A preferred such kit comprises hybridomas and/or monoclonal antibodies which they produce, e.g. the deposited cells referred to above and/or MAB 69/25 and/or MAB 71/3 which are optionally in labelled form (as is understood in the art), are immobilised on solid carriers or said kit contains labelling agents such as latex particles which may be coloured.

Two examples of preferred semi-defined medium are Medium (A) which consists solely of the components "Tryprose" (Oxoid Trade Mark) (e.g. 10–30 g/L, especially 20 g/L), Glucose (e.g. 0.5–2.0, especially 1.0 g/L), sodium chloride (e.g. 0.5–20. especially 9 g/L and agar (e.g. 5–25, especially 18 g/L) and Medium (B) which is particularly preferred and has the following composition, in which the proportions of components may vary by ±20%.

| MEDIA B | |
| --- | --- |
| Component | Grams/L |
| Hydrolysed Casein | 11.0 |
| Peptones | 3.0 |
| Dextrose | 2.0 |
| Sodium chloride (NaCl) | 3.0 |
| Soluble starch | 1.0 |
| Disodium hydrogen phosphate | 2.0 |
| Sodium acetate | 1.0 |
| Magnesium glycerophosphate | 0.2 |
| Calcium gluconate | 0.1 |
| Cobaltous sulphate ($CoSO_4$) | 0.001 |
| Cupric sulphate ($CuSO_4$) | 0.001 |
| Zinc sulphate ($ZnSO_4$) | 0.001 |
| Ferrous sulphate ($FeSO_4$) | 0.001 |
| Manganous chloride ($MnCl_2$) | 0.002 |
| Menadione | 0.001 |
| Cyanocobalamin | 0.001 |
| L-Cysteine hydrochloride | 0.02 |
| L-Tryptophan | 0.02 |
| Pyridoxine | 0.003 |
| Pantothenate | 0.003 |
| Nicotinamide | 0.003 |
| Biotin | 0.0003 |
| Thiamine | 0.00004 |
| Adenine | 0.01 |
| Guanine | 0.01 |
| Xanthine | 0.01 |
| Uracil | 0.01 |
| Agar No 1 | 8.0 |

A medium having this composition is sold by Oxoid under the trade name "Oxoid Iso-Sensitest Agar". The similar medium "Oxoid Sensitest Agar" is also preferred. The component "Tryprose" in Medium (A) is a commercially available product sold by Oxoid under the trade name "Tryprose". It has the following published composition:

| Component | Weight % |
| --- | --- |
| Water | 4.7 |
| Ash | 12.4 |
| Chloride (as NaCl) | 5.7 |

-continued

| Component | Weight % | |
|---|---|---|
| Phosphate (as P₂O₅) | | 1.2 |
| Total Nitrogen | | 12.7 |
| Amino Nitrogen | | 3.7 |
| Amino Nitrogen/Total Nitrogen | | 29.1 |
| Lipids | less than | 0.1 |
| Ammonia | | 0.84 |
| Lactose (by difference) | | — |
| Carbohydrate (as dextrose) | | — |
| pH of 2% solution (after autoclaving) | | 7.0 |
| Alanine | | 3.53 |
| Arginine | | 2.71 |
| Aspartate | | 6.15 |
| Cystine | | 0.40 |
| Glutamate | | 15.37 |
| Glycine | | 4.49 |
| Histidine | | 1.68 |
| Isoleucine | | 2.72 |
| Leucine | | 5.05 |
| Lysine | | 6.17 |
| Methionine | | 1.22 |
| Phenylalanine | | 2.83 |
| Proline | | 5.19 |
| Serine | | 0.86 |
| Threonine | | 1.66 |
| Tryptophan | | 0.86 |
| Tyrosine | | 1.78 |
| Valine | | 3.75 |
| Potassium | | 0.83 |
| Sodium | | 2.27 |
| Calcium | | 2220 ppm |
| Copper | | 2.25 ppm |
| Iron | | 68 ppm |
| Lead | less than | 2 ppm |
| Magnesium | | 706 ppm |
| Manganese | | 0.2 ppm |
| Tin | less than | 20 |
| Zinc | | 53 ppm |

It is expected that variation of ±30% of the concentration of any of the individual components of Tryprose will result in a medium of comparable usefulness in the method of the invention.

These media may be made up in an entirely convential way with distilled water and subsequently sterlised by autoclaving.

Growth of the Salmonella micro-organisms on the medium in the process of the invention may be under entirely standard conditions, e.g. by incubation at about 37° C. until a sufficient number of the micro-organisms having epitopic sites on their fimbriae have grown, for example typically by overnight incubation. An incubation temperature of above 22° C. is preferred for the effective production of the antigenic fimbriae bound by the monoclonal antibodies of the present invention. In applying the test in practice, a sample from a suspected material would be taken, containing a cross-section of all the micro-organisms present in the material, and these would then be grown on the medium so that Salmorella, if present, grows among any other micro-organisms that might be present. The presence of other micro-organisms does not seem to adversely affect the test. The test is further of use in the identification of the serotype of pure cultures of Salmonella organisms; ie: as S. enteritidis, S. dublin or other, further antibodies being usable to distinguish them further.

Procedures for raising both polyclonal and monoclonal antibodies to Salmonella surface antigens are well known. Thus, for example, S. enteritidis may be grown on a medium as described above so that antigenic fimbriae are produced, these then may be used to immunise mice from which spleen cells are subsequently isolated and fused with a myeloma cell line to form hybridomas. These hybridomas may then be seeded into microwells and monitored for antibody production, e.g. by ELISA or a similar technique. Antibody-producing hybridomas may then be cloned to produce a mouse monoclonal antibody to the Salmonella fimbrial antigen. MABs may be produced by the known method of intraperitoneally injecting hybridoma cells (e.g.; $10^6$) into mice and withdrawing ascites after 20 days; this can be used in crude form if necessary.

A particularly preferred monoclonal antibody is one having a specific immuno-affinity for the specific S. enteritidisfimbrial antigen (SEFA) produced by growth on one of the aforementioned media, ie. an antigenic protein fraction having a molecular weight of around 14,300 identified in the fimbrial structure after such growth conditions and having a major antigenic activity, or for immunoreactive (e.g. epitopic) parts or analogues thereof. The method and kits may employ polyclonal antibodies.

Examples of such monoclonal antibodies are those identified as MAB 69/25 and MAB 71/3 above and their use further extends to (i) the determination of media suitable for growing salmonella possessing the required antigenic fimbriae and (ii) for identification of said antigenic fimbriae and antigens comprising the SEFA epitope itself. Thus further specific media suitable for the performance of the method of the invention may be easily identified by screening salmonella grown in them for the ability to produce immunoagglutination with said MABs; a positive result indicating a suitable medium.

Either the whole Salmonella micro-organisms (live or dead) or a part thereof which includes the fimbrial antigen with the SEFA epitopic site may be detected by the antibody. In the latter case methods are well known, e.g. mild heat shock treatment at 60° C. for 30 minutes, for detaching fimbriae from Salmonella micro-organisms, and isolation of the fimbrial antigen in this way should lead to a more specific test result. The epitopic sites employed in the testing method of the preferred embodiment of the invention appear to be present on a fimbrial structure produced on the surface of S. enteritidis and S. dublin grown on media of the present invention and in vivo, which is less than 6 nm in diameter and consists of identical repeating subunits each of molecular weight between 14,000 and 15,000. These fimbriae have a 'kinked' conformation such that they entangle and extend in a matted form to approximately 200 nm from the cell surface. By applying size exclusion HPLC and SDS-PAGE to the fimbrial antigen isolated in such a way it has been determined that the principal antigenic protein employed appears to have a molecular weight of approximately 14,300. The sequence of isolated SEFA is given on page 20.

Exposure of the antigen to the antibody and the observation of the occurrence or otherwise of antibody-antigen binding may be carried out in ways which will be apparent to those skilled in the art of immunoassay. For example the whole micro-organisms may be exposed to a solution of the antibody for a suitable time, then after washing the micro-organisms may be exposed to a colloidal gold labelled second antibody. If the antibody is a mouse monoclonal this second antibody may, for example, be an anti-mouse Ig G. The binding of the antibody to the fimbriae may then be detected using microscopy to observe the clustering of gold particles around the fimbriae or said gold may have its visibility enhanced in known ways. Other suitable labels will occur to a man skilled in the art.

In another way immunoagglutination may be observed by simply adding a solution of the antibody to a solution or suspension of the microorganisms or to a culture thereof or to parts thereof such as the isolated fimbriae or the antigenic protein employed by the preferred embodiment of the invention. To assist in visualising immunoagglutination the antibody may be, labelled for example with coloured latex particles as is known in the art (Hechemy K E and Michaelson (1984) Lab Management 22 27–40).

In a further way, the antigen in the form of whole micro-organisms, the isolated fimbriae or isolated SEFA may be immobilised on a substrate such as a microtitre plate well, using known methods, then this immobilised antigen may be exposed to a solution of the antibody, then after washing a second labelled antibody capable of binding to the SEFA epitope unlabelled antibody may be applied (e.g.: a labelled anti-mouse Ig G) to the wells. After further washing detection of binding between this second antibody and the antibody itself bound to the immobilised antigen may then be observed by the presence of the bound label on the well. Other antibody/second antibody combinations will occur to the man skilled in the art (e.g. bovine or chicken antibodies/anti-bovine or anti-chicken second antibodies). Kits comprising free or immobilised SEFA or fimbriae are thus provided.

In a yet further way the antibody may be immobilised on a substrate and the immobilised antibody may then be exposed to a solution containing the antigen in the form of for example whole micro-organisms, the isolated fimbriae or the antigenic protein (SEFA), together with an agent capable of competing with the antigen for binding sites on the antibody. The quantity of the agent binding to the immobilised antibody may then be determined, e.g.: by use of known, labelling techniques. For example the competing agent may be a labelled anti-mouse IgG if the antibody is a mouse monoclonal, or may be labelled fimbrial antigen.

The labels used in the above methods may be entirely conventional, and ways of labelling antibodies are well known.

Other ways in which the testing method of the invention may be applied will be apparent to those skilled in the art, and the optimum way of applying it to any particular situation in which Salmonella organisms are to be tested for may vary. For speed and simplicity immunoagglutination is preferred, but for mope accurate or forensic work such techniques as the other alternatives suggested above may be preferred.

The testing method of the invention may be conveniently carried out using a test kit which may contain all or some of the reagents and other items for performance of the method of invention, for example the antibody, the medium visualising agents and standard result cards. Depending upon the way in which the test is to be applied the antibody may be provided in the form of a solution, e.g., for immunoagglutination or if the antigen is to be immobilised, or the antibody may be provided in the aforementioned immobilised form. The test kit may optionally also contain a second antibody, instructions and appropriate vessels for carrying out the test.

The various aspects of the invention will now be described by way of the following non-limiting protocol examples.

EXAMPLE I

Characterisation of SEFA and its epitope: production of MAB 69/25.
1. Bacterial strains and media.

The Salmonella strains examined are listed in Table I, and were obtained from the reference culture collection at the Central Veterinary Laboratory, Weybridge, Surrey, UK. Strains were stored on Dorset egg slopes and cultured in peptone water for 18 hours at 37° C. or 48 hours at 22° C.

2. Production of monoclonal antibodies.

A recent field isolate of *S. enteritidis* from a chicken (1246/89) was used to immunise BALB/c mice. The organisms were grown in peptone water overnight, centrifuged at 3000g for 10 min and resuspended in phosphate buffered saline (PBS) pH 7.2 to give an absorbance value of 1.25 at 400 nm (live antigen).

The same concentration of cells was also fixed in 1% formalin in PBS for 15 min (formalised antigen) or boiled for 1 hour (heat-killed antigen). Female mice, 6–8 weeks old were injected intra-peritoneally with 0.1 ml of either of the live or heat-killed antigens and three days later their spleens were removed for the production of monoclonal antibodies (MAB). Hybridomas were produced from the fusion between the BALB/c myeloma cell line N S1, and the murine splenocytes, following the protocol previously described ( Morris, J. A., Thorns, C. J. and Woolley, J. (1985) J. Gen. Microbiol. 131:1825–1831.). After cell fusion, hybridomas were seeded into 96-well micro-plates (Falcon 3072, USA) and monitored regularly for antibody production by an enzyme linked immunosorbent assay (ELISA) as detailed below. Selected hybridomas were expanded in RPMI 1640 medium (GIBCO Ltd, Glasgow, UK) containing penicillin (100 g/ml), streptomycin (100 units/ml), L-glutamine (1 mM) and foetal calf serum (20% v/v, Myoclone, GIBCO Ltd). Hybridomas secreting antibody were cloned by limiting dilution in the above medium supplemented with 10% (v/v) 20 BM-CONDIMED HI (Boehringer Mannheim, W. G.) and 0.1% mercaptoethanol (50 nM). Cloned and uncloned cell lines were frozen and stored in liquid nitrogen.

Culture supernatant from 293 microwells with hybridomas contained antibody that reacted with *S. enteritidis* antigens in the direct binding ELISA. Thirty-five of these bound exclusively to Salmonella antigens, and from these six stable unclonedhybridomas were secured in liquid nitrogen storage. Six clones were produced from hybridoma 69/25 and MAB produced by one of these recloned hybridomas was used for all further studies. The murine immunoglobulin was identified as subclass IgG1; and is referred to herein as MAB 69/25.

3- Direct binding immunoassays.

For detection of antibody producing hybridomas, microwell supernatants were tested for antibody to the live, formalised and heat killed antigens prepared from *S. enteritidis* using an indirect ELISA. Wells of polystyrene microtitration plates (NUNC F16, Denmark) were coated with 100 microliters of the antigens in 0.1M carbonatebicarbonate buffer pH 9.6 by incubation overnight at 37° C. The coated plates were washed four times with PBS containing 0.05% (v/v) Tween 20 (PBST) after which, free binding sites were blocked with 250 microliters/well of 1% (w/v) polyvinyl pyrollidone (Sigma, St Louis, U.S.A.) for 1 hour at 37° C. Culture supernatants from the fusion plates (50 microliters) were added to the wells, incubated at 37° C. for 1 hour and washed four times in PBST. An optimum dilution of goat anti-mouse IgG peroxidase conjugate (Cooper Biomedical, UK) was added (100 microliters/well) and incubated for 30 min at 37° C. AFter washing the plates four times in PBST, positive reactions were detected by the addition of 100 microliters/well of tetramethylbenzidine (Cambridge Veterinary Sciences, Cambridge, UK) For 15 min at room temperature, stopped with an equal volume of 10% (v/v) sulphuric acid. Optical densities were read at 490 nm (MR600, Dynatech Labs Ltd, UK).

Culture supernatants from selected hybridomas were tested against antigens from other genera of Enterobacteriaceae following the protocols described above for antigen production and direct binding ELISA. Monoclonal antibodies from cloned hybridomas were examined further in the direct binding ELISA for their ability to bind to the organisms listed in Table I. Organisms were grown and standardised using the procedure described above for the preparation of *S. enteritidis* live antigen. Results were expressed as the percentage of antibody binding to the test antigens relative to the binding in the high control in which normal mouse serum (Miles Laboratories, UK) was used in place of antigen.

4. Isolation and fractionation of cell surface antigens.

*S. enteritidis* strain 468/86 (strong binding by MAB 69/25 in ELISA) was grown overnight in 5 L of Slanetz broth, a medium consisting of 20 g/L "Tryprose" (Oxoid). 1 g/L glucose, 9 g/L sodium chloride and 18 g/L Agar, (ie Medium (A) above) at 37° C. The cells were sedimented at 3000 g and resuspended in 100 ml of PBS pH 6.8 containing 0.1% (w/v) protease-free bovine serum albumin (Sigma. St Louis. U.S.A.). The cell suspension was heat shocked at 60° C. for 30 mins, while shaking gently and the cell free supernatant applied to a size exclusion HPLC column (TSK-G 3000 SW, Japan) in 0.2M phosphate buffer pH 7.5 at a flow rate of 2 ml/min. Fractions (2 ml) were collected and examined for antigenic activity in the direct binding ELISA.

Maximum binding of MABs occurred with fractions from the first peak eluted from the HPLC gel filtration column containing antigen fragments of about 600,000 molecular weight. SDS-PAGE on prefractionated material and fractions from this peak demonstrated the purification of a major protein band which corresponded to the molecular weight standard of 14,300. Western blots were performed on the crude and semipurified material and probed with MAB 69/25. In both preparations only one band was detected, which corresponded to the 14,000 molecular weight standard. When MAB 69/25 was omitted in the test procedure no bands were detected.

Antigens in the crude and purified extracts of the *S. enteritidis* surface material were separated in 12.5% SDS-PAGE gels using a discontinuous tris-HCl buffer system under reducing conditions (Laemmli, U.K. 1970. Nature (London) 227:680–685). Gels were stained with Coomassie brilliant blue R250, and protein bands compared with molecular weight standards run in parallel (Sigma, St Louis, U.S.A.).

Separated antigens were transferred from an SDS-PAGE gel to a nitrocellulose membrane by electroblotting at 110 mA overnight in a tris-glycine-methanol transfer buffer (Towbin, H., T. Staehelin, and J. Gordon 1979. Proc. Natl. Acad. Sci. USA 76: 4350–4354). After drying, the membrane was saturated with 3% (w/v) bovine serum albumin for 1 hour followed by three 10 min washes in PBST. Antigens on the membrane were probed for 1 hour at 37° C. with MAB 69/25 diluted in PBST containing 1% (w/v) bovine serum albumin, followed by three 10 min washes in PBST. Binding of MAB to antigens was detected by incubation with affinity purified, biotinylated sheep anti-mouse Ig species-specific F(Ab')$_2$ fragment (Amersham International, UK) for 1 hour at 37° C., followed by three 10 min washes in PBST and incubation for 30 min at 37° C. with streptavidin biotinylated horseradish peroxidase complex (Amersham International, UK). After washing three times in PBST the reaction was revealed with 0.5% (w/v) chloronaphthol and 0.015% (w/v) hydrogen peroxide as substrate.

5. Conventional and immune electron microscopy.

This was undertaken to locate the antigen recognised by MAB 69/25. Salmonella strains were grown overnight in peptone water at 37° C. or 22° C. and the cells were centrifuged, washed once and resuspended in PBS. A carbon Formvarcoated grid was floated on 1 drop of antigen supension for 5 min at room temperature and after removal of excess liquid, floated on 2% (v/v) phosphotungstic acid (PTA) pH6.6 for 2 min. Dried grids were examined in a Philips EM410LS electron microscope operating at 80 KV.

For immune electron microscopy antigen coated grids were floated on 1 drop of an optimum dilution of MAB 69/25 for 15 min at room temperature. They were washed three times in PBST and then floated on 1 drop of goat anti-mouse IgG labelled with 5 nm diameter gold particles (Janssen Autoprobe RTM, Belgium) diluted in PBST for 15 min at room temperature. Grids were washed three more times in PBST and stained and examined as described above.

Transmission electron microscopy of *S. enteritidis* 1246/89 (fusion strain) cultured for 18 hours at 37° C. revealed three identifiable types of surface organelles. The majority of organisms expressed flagellae, as well as a 'rigid', straight type 1 fimbriae measuring up to 300 nm in length and 8 nm in diameter, projecting from the cell surface. The number of fimbriae on each bacterial cell was variable, and some organisms were devoid of any. A fine fibrillar material attached, usually uniformly, around the bacterium was also observed. Individual filaments within this material were difficult to visualise, measuring less than 5 nm in diameter. Filaments had a 'kinked' conformation such that they entangled with each other to form a matted appearance. The matted fibrils extended from the cell surface to approximately 200 nm within the limit of the pool of negative stain around each cell. When the same strain of *S. enteritidis* was incubated with MAB 69/25 and immunogold conjugate, the fimbrial material was labelled heavily with gold particles. Once labelled this antigen could be seen to extend up to 0.1 micrometers from the cell surface, and was also found in detached amorphous clumps.

Flagellae and type 1 fimbriae were unlabelled. Two further *S. enteritidis* strains and three *S. dublin* strains that reacted in the direct binding ELISA, also expressed this fimbrial material which was specifically labelled with the MAB, although many *S. dublin* organisms appeared within a population not to express this structure or epitope. Fimbrial antigen was not detected or labelled when the same strains of *S. enteritidis* and *S. dublin* were grown at 22° C. Strains of *S. gallinarum*, *S. pullorum* and *S. typhimurium* grown at 37° C. for 24 hr were not labelled with gold after probing with Mab.

6. Conclusion.

The above experiments illustrate the identification of a specific antigen located on the fimbriae of strains of *S. enteritidis* grown on Slanetz broth, a semi-defined medium, at 37° C., and the raising of a specific monoclonal antibody MAB 69/25 to this antigen. Tests show that MAB 69/25 binds only to certain Salmonella serotypes within serogroup D. These results were extended and confirmed when a further 264 Salmonella strains from 63 serotypes were examined. All the strains of *S. enteritidis* tested, regardless of phage type, reacted with this MAB. *S. dublin* (12/36 strains) and the one strain of *S. moscow* tested were the only other serotypes that were positive.

Electron microscope studies confirmed that MAB 69/25 is directed against an epitope on a fimbrial structure expressed on the bacterial surface that is morphologically distinct from flagellae and the larger type 1 fimbriae. This structure was observed only on Salmonella strains that reacted in direct binding ELISAs and these strains were labelled when examined by immune EM.

This fimbrial structure is much smaller than the type 1 fimbriae commonly found on Salmonella strains (Clegg et al above), and unlike type 3 fimbriae carried by Salmonellae, it lacks any haemagglutinating activity (Clegg et al above; Abegbola, R. A., D. C Old and S. Aleksic 1983. FEMS Microbiol. Lett. 19: 233–238; Old. D. C., and R. A. Adegbola, 1985. J. Med. Microbiol. 20: 113–121). This fimbrial structure, which carries an epitope restricted to all strains of *S. enteritidis* and certain strains of *S. dublin* and *S. moscow* (see Tables I and II) differs from all previously described Salmonellae structures.

It will be appreciated that SEFA, as described above and by the amino acid sequence below, contains epitopic sites such that parts of it, ie. fragments, will be similarly specifically antigenic. Suitable fragments will be readily determinable by a man skilled in the art using conventional immunological tests. For example, the antigen may be hydrolysed or ezymically cleaved to provide a variety of oligopeptides which may be sequenced and tested for agglutination with the provided antibodies MAB 69/25 or MAB 71/3 or other antibodies raised against SEFA. Such determination would involve no undue experimentation or inventive input. Thus the present invention encompasses the use of such epitopic parts of SEFA in place of SEFA itself for all the uses described herein.

Furthermore, it is possible to combine SEFA or an epitopic part thereof with other antigens or epitopes. Such combination antigens are exemplified in copending MAFF application Ser. No. 08/030,383 filed Mar. 31, 1993 of inventor M. Woodward and these similarly may be used in place of SEFA itself for all the uses described herein. Natural allelic variants of SEFA are to be expected and these, in so far as they contain the epitopic sites of the SEFA identified herein, are clearly usable instead of it in all the present uses of the invention.

AMINO ACID SEQUENCE OF SALMONELLA ENTERIDITIS FIMBRIAL ANTIGEN (SEFA).

```
M L I V D F W R F C N M R K S A S A V A V L A L I A C G S A H A A G
F V G N K A E V Q A A V T I A A Q N T T S A N W S Q D P G F T G P A
V A A G Q K V G T L S I T A T G P H N S V S I A G K G A S V S G G V
A T V P F V D G Q G Q P V F R G R I Q G A N I N D Q A N T G I D G L
A G W R V A S S Q E T L N V P V T T F G K S T L P A G T F T A T F Y
V Q Q Y Q N
SEQ ID NO: 1
```

The codes above are standard codes. Amino terminal to Carboxy terminal: left to right; M to N. according to the following key:

| Amino acid | |
|---|---|
| Alanine | A |
| Arginine | R |
| Asparagine | N |
| Aspartic acid | D |
| Cysteine | C |
| Glutamic acid | E |
| Glutamine | Q |
| Glycine | G |
| Histidine | H |
| Isoleucine | I |
| Leucine | L |
| Lysine | K |
| Methionine | M |
| Phenylalanine | F |
| Proline | P |
| Pyroglutamyl | *E |
| Serine | S |
| Threonine | T |
| Tryptophan | W |
| Tyrosine | Y |
| Valine | V |

TABLE I

264 Salmonella strains examined with monoclonal antibody MAB69/25

| Serogroup | Serotype (No. strains tested) |
|---|---|
| B | *S. agama* (1) |
| | *S. agona* (1) |
| | *S. bredeney* (1) |
| | *S. derby* (1) |
| | *S. heidelberg* (1) |
| | *S. indiana* (1) |
| | *S. reading* (1) |
| | *S. schwarzengrund* (1) |
| | *S. stanley* (1) |
| | *S. typhimurium* (64) |
| C1 | *S. bareilly* (1) |
| | *S. infantis* (1) |
| | *S. lille* (1) |
| | *S. livingstone* (1) |
| | *S. mbandaka* (1) |
| | *S. montevideo* (1) |
| | *S. ohio* (1) |
| | *S. oranienburg* (1) |
| | *S. oslo* (1) |
| | *S. thompson* (1) |
| | *S. virchow* (1) |
| C2 | *S. goldcoast* (1) |
| | *S. hadar* (1) |
| | *S. newport* (1) |
| C3 | *S. albany* (1) |

TABLE I-continued

264 Salmonella strains examined with monoclonal antibody MAB69/25

| Serogroup | Serotype (No. strains tested) |
|---|---|
| | *S. kentucky* (2) |
| | *S. tado* (1) |
| D1 | *S. berta* (1) |
| | *S. canastel* (1) |
| | *S. dublin* (36) |
| | *S. durban* (1) |
| | *S. enteritidis* (58) |
| | *S. gallinarium* (44) |
| | *S. moscow* (1) |
| | *S. ouakam* (1) |
| | *S. panama* (1) |
| | *S. pullorum* (3) |
| | *S. wangata* (1) |
| E1 | *S. anatum* (1) |

TABLE I-continued

264 Salmonella strains examined with monoclonal antibody MAB69/25

| Serogroup | Serotype (No. strains tested) |
|---|---|
|  | S. give (1) |
|  | S. lexington (1) |
|  | S. london (1) |
|  | S. meleagridis (1) |
|  | S. nchanga (1) |
|  | S. orion (1) |
| E2 | S. binza (1) |
|  | S. drypool (1) |
|  | S. manila (1) |
|  | S. newington (1) |
| E4 | S. taksony (1) |
|  | S. senftenberg (1) |
| F | S. aberdeen (1) |
| G1 | S. havana (1) |
|  | S. worthington (1) |
| G2 | S. ajiobo (1) |
|  | S. kedougou (1) |
| K | S. cerro (1) |
| N | S. urbana (1) |
| O | S. adelaide (1) |
|  | S. ealing (1) |
| R | S. johannesburg (1) |
| S | S. offa (1) |
| T | S. gera (1) |

TABLE II

Direct binding of MAB 69/25 to Salmonella strains

| Serotype |  | Number Examined | Monoclonal antibody MAB 69/25 % bound | |
|---|---|---|---|---|
| S. enteritidis | PT 1 | 2 | 56[a] | (48–64)[b] |
| S. enteritidis | PT 4 | 22 | 57 | (14–100) |
| S. enteritidis | PT 4 plasmid minus | 6 | 57 | (49–65) |
| S. enteritidis | PT 5 | 1 | 83 | |
| S. enteritidis | PT 6 | 1 | 57 | |
| S. enteritidis | PT 7 | 1 | 89 | (85–93) |
| S. enteritidis | PT 8 | 12 | 53 | (15–90) |
| S. enteritidis | PT 9 | 4 | 20 | (17–23) |
| S. enteritidis | PT 11 | 7 | 50 | (23–77) |
| S. enteritidis | PT 30 | 1 | 15 | |
| S. enteritidis untypable |  | 1 | 41 | |
| S. dublin |  | 12 | 25 | (9–40) |
| S. dublin |  | 24 | 0 | |
| S. moscow |  | 1 | 9 | |
| Other Salmonella strains[c] |  | 169 | 0 | |

[a]Mean percentage of antibody binding relative to binding to high control (see text)
[b]Range of binding
[c]Serotypes listed in Table II
PT = Phage type

EXAMPLE II

Assessment of various media for the ability to support expression of Salmonella enteritidis fimbrial antigen (SEFA).

1. Salmonella strains and media.

The strains examined in this example are listed in Table III and were obtained from the reference culture collection at the Central Veterinary Laboratory, Weybridge, Surrey, United Kingdom, and stored on Dorset egg slopes.

The liquid media used to grow strains were: Enriched E broth (Francis, D. H. et al. (1982) J. Clin. Microbiol. 15: 181–183); Heart Infusion broth (Oxoid Unipath, Basingstoke, United Kingdom); Minca Broth (Guinee, P. A. M. et al, (1976) Infect. Immun. 13: 1369–1377); peptone water pH 6.0 and 7.2, Slanetz broth (Ness, E. (1983) Acta. Vet. Scand. 24: 521–523) and Vogel Bonner medium.

The following solid media were also used: Bismuth Sulphite agar (Difco, East Molesey, United Kingdom), Brilliant Green agar (Oxoid), Desoxycholate Citrate agar (Oxoid), McConkey agar (Oxoid), Nutrient agar (Oxoid), Salmonella Shigella agar (Oxoid), Sensitest and Isosensitest agar (Oxoid), 5% Sheep Blood agar (Difco), and Xylose Lysine Desoxycholate agar (Difco).

Strains were cultured in liquid or solid medium for 18hours at 37° C.

MABS.

The MABS used in latex tests were produced and characterised as above and were coated onto latex particles using the standard methods described by Hechemy et al (as above). Briefly, an optimum concentration of MAB in ascites was added to a 10% (w/v) suspension of 0.8 micron diameter blue latex particles (Code K080, Estapor, Rhone-Poulenc Laboratory, Manchester, United Kingdom), and 0.1M glycine buffered saline (GBS) pH 8.2 in an approximate ratio of 1:30:120 and incubated for 2 h at 37° C. with constant gentle rocking. The coated latex was then washed and suspended in GBS pH 8.2 containing 0.1% fatty acids-free bovine serum albumin (Sigma Chemical Co., St. Louis, Mo.) to a final concentration of 0.25% (w/v). The latex reagents were stored at 4° C. Control latex reagents were prepared by replacing MABs with normal mouse serum obtained from 8 to 10 week-old female BALB/c mice.

Latex agglutination test.

Tests were carried out by mixing equal volumes (50 microliters) of latex reagent and suspensions of organisms in GBS pH 8.2 or directly from the broth culture on a disposable white plastic-coated card, rocking gently for up to four minutes and observing any macroscopic agglutination. Auto agglutination of test suspensions were checked by replacing the MAB-coated latex with the control latex.

The performance of the latex reagent was monitored regularly using positive control antigen preparations in place of test organisms.

MAB-coated latex reagents.

The reagents were tested for their ability to agglutinate with cell-free SEFA and with a panel of salmonellae and other related bacteria. The latex reagent coated with SEFA-9 MAB (TABLE VI) was specific and the most sensitive (data not shown) and was used for all further studies.

Effect of-growth media on SEFA expression using latex particle agglutination.

The expression of SEFA by S. enteritidis grown in different culture media is described in Table IV. The six S. enteritidis strains used, were selected to represent high and low producers of SEFA when the organisms were grown in peptone water pH 7.2 at 37° C. Peptone water pH 7.2 and Enriched E broth were the only liquid media where SEFA was detected on all six S. enteritidis strains (Table IV). However, when the strains were grown in peptone water pH 7.2 they agglutinated more strongly than they did following growth in Enriched E broth. Conversely, when the strains were grown in MINCA medium, Vogel Bonner and Heart Infusion broth very little SEFA was produced as evidenced by little or no agglutination with the latex reagent (Table IV). The addition of a further 0.1% (w/v) glucose to all the liquid media reduced considerably the production of SEFA by the strains. All six strains of S. enteritidis grown on nutrient agar and 5% sheep blood agar agglutinated with the MAB-coated latex, but the strains agglutinated most strongly when grown on Sensitest of Isosensitest agar (Table IV). When strains were cultured on common Salmonella isolation and selection media the expression of SEFA was reduced and in the case of Brilliant Green and Bismuth Sulphite agars completely inhibited (Table IV).

Detection of SEFA on Salmonella strains using latex particle agglutination.

Two hundred and eighty Salmonella strains representing 120 serotypes from 24 serogroups were grown on Sensitest agar for 18 hours at 37° C., and examined for SEFA production by latex agglutination (Table V). All the *S. enteritidis* (64) and the majority of *S. dublin* strains (28/33) tested agglutinated the latex reagent. The single representative strains of *S. blegdam* and *S. moscow* also agglutinated the reagent. No other strains from serotypes within serogroup D or any other serogroup examined agglutinated the latex.

DISCUSSION

Of the liquid and solid media tested in this study, peptone water pH 7.2 and Sensitest or Isosensitest (Oxoid) were the media of choice. When the Salmonella strains were grown on Sensitest (Oxoid) agar for 18hour at 37° C. SEFA was detected on all the *S. enteritidis* strains (64) and the majority of *S. dublin* strains (28/33). Single isolates from only two other serotypes *S. blegdam* and *S. moscow* produced SEFA. Both these serotypes which are very closely related to *S. enteritidis*, are extremely rare and have not been seen by the CVL's reference laboratory since the Zoonoses Order (1975) started in the United Kingdom in 1976. The detection of strains expressing SEFA is therefore an indication of *S. enteritidis* or *S. dublin*, and on isolates originating from poultry products can be regarded as a presumptive identification of *S. enteritidis*.

TABLE III

| Salmonella strains examined by latex agglutination[a] | | |
|---|---|---|
| Serogroup (No. tested) | | |
| B | | S. agama (1) |
| | | S. agona (3) |
| | | S. bredeney (2) |
| | | S. california (1) |
| | | S. chester (1) |
| | | S. coeln (1) |
| | | S. derby (2) |
| | | S. heidelberg (4) |
| | | S. indiana (3) |
| | | S. massenya (1) |
| | | S. reading (2) |
| | | S. saint paul (1) |
| | | S. san diego (1) |
| | | S. schwarzengrund (1) |
| | | S. stanley (1) |
| | | S. stanleyville (1) |
| | | S. typhimurium (23) |
| C1 | | S. amersfoort (1) |
| | | S. bareilly (1) |
| | | S. brandenberg (1) |
| | | S. infantis (3) |
| | | S. hartford (1) |
| | | S. lille (1) |
| | | S. livingstone (2) |
| | | S. mbandaka (2) |
| | | S. montevideo (2) |
| | | S. oakland (1) |
| | | S. ohio (2) |
| | | S. oranienburg (2) |
| | | S. oslo (1) |

TABLE III-continued

| Salmonella strains examined by latex agglutination[a] | |
|---|---|
| Serogroup (No. tested) | |
| | S. singapore (1) |
| | S. tennessee (6) |
| | S. thompson (1) |
| | S. virchow (2) |
| C2 | S. bovis morbificans (1) |
| | S. goldcoast (1) |
| | S. hadar (3) |
| | S. kottbus (1) |
| | S. manhattan (1) |
| | S. meunchen (1) |
| | S. nagoya (1) |
| | S. newport (2) |
| C3 | S. albany (1) |
| | S. bardo (1) |
| | S. emek (1) |
| | S. haardt (1) |
| | S. kentucky (1) |
| | S. molade (1) |
| | S. tado (1) |
| C1 | S. berta (6) |
| | S. blegdam (1) |
| | S. canatel (1) |
| | S. dublin (33) |
| | S. durban (1) |
| | S. eastbourne (1) |
| | S. enteritidis (64) |
| | S. fresno (1) |
| | S. gallinarum (3) |
| | S. kapemba (1) |
| | S. miami (1) |
| | S. moscow (1) |
| | S. napoli (1) |
| | S. oukam (1) |
| | S. pullorum (1) |
| | S. wangata (1) |
| E1 | S. amsterdam (1) |
| | S. anatum (3) |
| | S. butantan (1) |
| | S. falkensee (1) |
| | S. lexington (1) |
| | S. london (1) |
| | S. meleagridis (2) |
| | S. meunster (1) |
| | S. nchanga (1) |
| | S. orion (3) |
| | S. regent (1) |
| | S. uganda (1) |
| | S. vejle (1) |
| | S. weltevreden (1) |
| | S. westhampton (1) |
| E2 | S. binza (2) |
| | S. drypool (1) |
| | S. manila (1) |
| | S. newington (1) |
| E3 | S. wildwood (1) |
| E4 | S. liverpool (1) |
| | S. llandoff (1) |
| | S. senftenberg (3) |
| | S. taksony (2) |
| F | S. bullbay (1) |
| | S. chandans (1) |
| | S. telhashomer (1) |
| G1 | S. havana (1) |
| | S. poona (1) |
| G2 | S. ajiobo (1) |
| | S. cubana (1) |
| | S. idikan (1) |
| | S. kedougou (2) |
| H | S. fischerkeitz (1) |
| I | S. chameleon (1) |
| | S. gaminara (1) |
| | S. tees (1) |
| K | S. cerro (1) |
| M | S. pomona (1) |

TABLE III-continued

Salmonella strains examined by latex agglutination[a]

| Serogroup | (No. tested) |
|---|---|
| N | S. godesberg (1) |
|   | S. urbana (1) |
| O | S. adelaide (1) |
|   | S. alachua (1) |
|   | S. ealing (1) |
|   | S. widemarsh (1) |
| Q | S. anfo (1) |
|   | S. wandsworth (1) |
| R | S. johannesberg (1) |
|   | S. millesi (1) |
|   | S. omifisan (1) |
| S | S. offa (1) |
| T | S. gera (1) |
|   | S. toricada (1) |
| X | S. bergen (1) |
| Y | S. marina (1) |

[a]Two hundred and eighty Salmonella strains were examined.

TABLE IV

Effect of growth medium on the production of SEFA fimbrial antigen by Salmonella enteritidis strains using latex agglutination[a]

| Growth medium | S. enteritidis strains | | | | | |
|---|---|---|---|---|---|---|
|  | A | B | C | D | E | F |
| Liquid: | | | | | | |
| Enriched E broth | + | + | + | + | + | + |
| Heart Infusion broth | ++ | + | − | − | + | + |
| MINCA broth | − | − | − | − | − | − |
| Peptone water pH 7.2 | ++ | ++ | ++ | ++ | ++ | +++ |
| Peptone water pH 6.0 | ++ | ++ | ++ | − | ++ | +++ |
| Slanetz | ++ | ++ | + | − | + | + |
| Vogel Bonner | + | − | − | − | − | − |
| Solid: | | | | | | |
| Brilliant Green | − | − | − | − | − | − |
| Bismuth Sulphite | − | − | − | − | − | − |
| Desoxycholate Citrate | ++ | ++ | ++ | + | ++ | +++ |
| McConkey | ++ | ++ | + | + | ++ | +++ |
| Nutrient | ++ | ++ | ++ | ++ | ++ | +++ |
| Salmonella Shigella | ++ | ++ | ++ | ++ | ++ | +++ |
| Sensitest (Isosensitest) | +++ | +++ | +++ | +++ | +++ | +++ |
| Sheep blood | ++ | ++ | ++ | ++ | ++ | +++ |
| Xylose Lysine-Descholate | ++ | ++ | ++ | + | ++ | +++ |

[a]+, agglutinates 3–4 min; ++; agglutinates 1–3 min; +++, agglutinates ≦ 1 min.
−, negative.

TABLE V

Detection of SEFA fimbrial antigen on Salmonella strains by the latex agglutination test.

| Serotype | No. of strains examined | Latex agglutination test + | Latex agglutination test − |
|---|---|---|---|
| S. enteritidis | 64 | 64 | — |
| S. dublin | 33 | 28 | 5 |
| S. blegdam | 1 | 1 | — |
| S. moscow | 1 | 1 | — |
| Other Salmonella strains[a] | 181 | — | 181 |

[a]Serotypes listed in Table IV.

EXAMPLE II

Latex test kit and protocol for use:

Kit comprises MAB 71/3, reader cards and preferred growth medium optionally with any of the reagents (e.g. latex particles) below used in the test.

1. Preparation a batch of suspension buffer (GBS)

Materials: Glycine (Koch-light Ltd, Anolov), Sodium chloride (BDH) Sodium hydroxide (BDH), Kathon CG (Rohm and Haas) via Chesham Chemicals, Deionised water, 0.2 micron membrane filters (bottle top, Falcon), Dropper bottles, Pressmatic dispenser (Bibby), Labels, Glass container suitable for batch size, pH meter, Stirrer.

Preparation Volumes (0.1M glycine, 0.1M NaCl, 0.1% Kathon, pH 8.2)

| 1 Batch size ml | 2 Deionised water ml | 3 Glycine g | 4 NaCl g | 5 Kathon ml | 6 6M NaOH ml | 7 Bottle No. |
|---|---|---|---|---|---|---|
| 1000 | 800 | 7.5 | 5.85 | 1.0 | 0.3 | 100 |
| 2000 | 1800 | 15.0 | 11.70 | 2.0 | 0.6 | 200 |
| 5000 | 4700 | 37.5 | 29.25 | 5.0 | 1.5 | 500 |
| 10000 | 9700 | 75.0 | 58.5 | 10.0 | 3.0 | 1000 |

Measure pH of the solution and add 6M sodium hydroxide dropwise, stirring continuously until pH is 8.2. Volumes of NaOH in Column 5 are only approximate. Top up with deionised water to the volume of the chosen batch size. Filter into sterile container using 0.2 ml filter. Dispense asceptically into dropper bottles a volume of 10.0 ml using the pressmatic dispenser. Store at +4° C.

2. Coating of anti-SEFA latex (TEST LATEX 1).

To prepare a batch of latex coated with M71/3 anti-SEFA monoclonal antibody.

Materials:

Glycine bufferred saline (GBS as above), Bovine serum albumen (fatty acids free) (Code A-6003, Sigma Chemicals), Blue latex, 0.8 microns, 10% suspension (Code K080, Estapor, Rhone-Poulene), Monoclonal antibody MAB 71/3 ascetic fluid batch 1, Glass container of the suitable size—Pressmatic dispenser (Bibby)—Dropper bottles—Labels—Rocking device Preparation:

Volumes (Every new batch of antibody has to be titrated to find optimal volumes for coating of latex).

| Blue latex ml | Ascitic fluid b.1 ml | GBS ml | Batch size ml | Bottle No |
|---|---|---|---|---|
| 1.5 | 0.05 | 6.0 | 60.0 | 10 |
| 3.0 | 0.1 | 12.0 | 120.0 | 20 |
| 7.5 | 0.25 | 30.0 | 300.0 | 50 |
| 15.0 | 0.5 | 60.0 | 600.0 | 100 |
| 37.5 | 1.25 | 150.0 | 1500.0 | 250 |

Method:

(i) Choose the batch size (volume) of latex to be prepared (ii) Mix volumes of latex, antibody and GBS appropriate for that batch size in a glass container and incubate for 2 hours at 37° C. with constant gentle rocking, (iii) Centrifuge for 20 minutes at 3500 rpm. (iv) Discard supernatant and resuspend latex in appropriate volume of GBS containing 0.1% BSA.

Dispensing and labelling:

(i) Dispense asceptically into dropper bottles a volume of 6.0 ml using clean pressmatic dispenser. (ii) Add plugs and ensure that the temper-evident lid is screwed on TIGHTLY. iii) Label the bottles with the appropriate labels and store at +4° C.

3. Coating of Test Latex 2 (rabbit polyclonal against *S. dublin*).

To prepare a batch of latex coated with rabbit polyclonal serum against flagella of *S. dublin*.

Materials:

The polyclonal serum is prior absorbed with *S. enteritidis* to remove all antibody crossreacting with it. Glycine buffered saline (GBS); Bovine serum albumin (fatty acids free) Code A-6003, Sigma Chemicals; Red latex, 0.8 microns, 10% suspension Code K080, Estapor, Rhone-Poulene; Rabbit serum specific to *S. dublin* p antigen; Glass container; Pressmatic dispenser (Bibby); Dropper bottles; Labels: Rocking device.

Preparation Volumes, every new batch of antibody has to be titrated to determine optimal volumes for coating.

| Red latex ml | Antibody ml | GBS ml | Batch size ml | Bottle No. |
|---|---|---|---|---|
| 1.5 | 0.5 | 6.0 | 60.0 | 10 |
| 3.0 | 1.0 | 12.0 | 120.0 | 20 |
| 7.5 | 2.5 | 30.0 | 300.0 | 50 |
| 15.0 | 5.0 | 60.0 | 600.0 | 100 |
| 37.5 | 12.5 | 150.0 | 1500.0 | 250 |

Method:

(i) Choose the batch size (volume) of latex to be prepared (ii) Mix volumes of latex, antibody and GBS in a glass container and incubate for 2 hours at 37° C. with constant gentle rocking. (iii) Centrifuge for 20 minutes at 3500 rpm. (iv) Discard supernatant and resuspend latex in appropriate volume of GBS containing 0.1% BSA.

Dispensing and labelling:

(i) Dispense asceptically into dropper bottles a volume of 6.0 ml using clean pressmatic dispenser. (ii) Add plugs and ensure that the temper-evident lid is screwed on TIGHTLY. (iii) Label the bottles with the appropriate labels and store at +4° C.

5. Control latex

To prepare a batch of control latex.

Materials:

Glycine buffered saline (GBS); Bovine serum albumin (fatty acids free) Code A-6003, Sigma Chemicals; Blue latex; 0.8 microns, 10% suspension Code K080, Estapor, Rhone-Poulene; Normal mouse serum collected from 8–12 weeks old Balb/c mice; Glass container; Pressmatic dispenser (Bibby); Dropper bottles; Labels; Rocking device.

Preparation:

Volumes

| Blue latex (ml) | Antibody Mouse Serum | GBS ml | Batch size ml | Bottle No. |
|---|---|---|---|---|
| 1.5 | 0.05 | 6.0 | 60.0 | 10 |
| 7.5 | 0.25 | 30.0 | 300.0 | 50 |
| 15.0 | 0.5 | 60.0 | 600.0 | 100 |
| 37.5 | 1.25 | 150.0 | 1500.0 | 250 |

Method:

(i) Choose the batch size (volume) of latex to be prepared. (ii) Mix volumes of latex, normal mouse serum and GBS appropriate for chosen batch size in a glass container and incubate for 2 hours at 37° C. with constant gentle rocking. (iii) Centrifuge for 20 minutes at 3500 rpm. (iv) Discard supernatant and resuspend latex in appropriate volume of GBS containing 0.1% BSA Dispensing and labelling:

(i) Dispense asceptically into dropper bottles a volume of 6.0ml using clean pressmatic dispenser. (ii) Add plugs and ensure that the temper-evident lid is screwed on TIGHTLY. (iii) Label the bottles with the appropriate labels and store at +4° C.

5. Positive control antigen 1:

To prepare a batch of positive control antigen to agglutinate with TEST LATEX 1.

Materials:

*S. enteritidis* strain 486/86—Sensitest agar plates (Media room); 1% Formalin in phosphate buffered saline 0.1M pH 7.2; GBS.

Method:

(a) Inoculate 20 Sensitest agar plates and incubate 24 hours at 37° C. (b) Harvest the growth into 40 ml of 1% formalin buffer and incubate for 3 hour at 37° C. (c) Determine the titre as the reciprocol of the highest dilution giving complete agglutination with TEST LATEX 1. The titre should be at least 1:500. Store cells frozen at −20° C. (d) On the day of preparing a batch determine the working strength of the reagent as three dilutions above the titre (e.g. latex titre 1:1027, working dilution 1:256). (e) Dilute the cells in GBS to working strength.

\* To determine the volume of the cells suspension to be diluted with GBS divide batch size (ml) by reciprocol of the latex titre. If to prepare 600 ml of cell suspension with 1/128 latex titre add 4.7 ml of cells to 595.3 ml of GBS.

Dispensing and labelling:

i) Dispense asceptically into dropper bottles a volume ml using pressmatic dispenser. (ii) Add plugs and ensure that the temper-evident lid is screwed on TIGHTLY. (iii) Label the bottles with the appropriate labels and store at +4° C.

Positive control/antigen 2.

To prepare a batch of positive control antigen to agglutinate with TEST LATEX 2.

Materials:

Second *S. dublin* strain: BAB No.2. Lact+NR agar plates; GBS; Craigie Tubes; 10 ml lots of Peptone broth; PBS pH7.2; Formaldehyde; Biohazard cabinet.

Method:

(a) Inoculate stock culture onto BAB No2. +LACT+NR. Incubate overnight at 37° C. (b) Select a well isolated smooth colony, use about half to confirm the identity of the organism by tube agglutination. When satisfied use remainder of colony to inoculate a "straight" Craigie tube. Incubate overnight at 37° C. (c) When growth reaches the upper surface of the Craigie tube examine by "hanging drop" for hypepermotility. If not evident continue by inoculating a fresh Craigie from this one. When hyper motility is achieved—usually 2–3 passages—proceed as follows:

(d) Inoculate hypermotile culture into sufficient number of prewarmed 10 ml amounts of peptone broth for quantity of plates required. Inucbate peptone broth cultures for 2 hours at 37° C. Use 1 ml amounts to inoculate undried Sensitest aqarplates, ensure that entire surface is covered. Incubate overnight at 37° C. lid uppermost. (e) In biohazard cabinet harvest cells from plates using 2 ml PBS DH7.2 per plate. Use further 2 ml PBS to recover residual cells. (f) Add formaldehyde to give final concentration 0.3%. (g) Determine the titre as the reciprocol of the highest dilution giving complete agglutination with TEST LATEX 2. The titre should be at least 1:10. Store cells frozen at −20° C. (h) On the day of preparing a batch determine the working strength of the reagent as two dilutions above the titre. Dilute the cells in GBS to working strength.

Dispensing and labelling:

i) Dispense asceptically into dropper bottles a volume using pressmatic dispenser. (ii) Add plugs and ensure that the temper-evident lid is screwed on TIGHTLY. (iii) Label the bottles with the appropriate labels and store at +4° C.

Use:

Samples exposed to test latexes are compared with controls usind reader cards. the test latex 1 is used to identify presence of SEFA bearing materials (e.g.; whole organisms). Test latex 2 is used to differentiate *S. enteritidis* and *S. dublin,* the latter only binding to it. The control latex aids determination of false positives caused by, inter alia, autoagglutination. The positive control and reader cards are used to determine degree of response.

EXAMPLE IV

Use of various MABs to characterise SEFA.

Bacterial strains and media.

Salmonella strains examined in the present study which were obtained from the reference culture collection at the Central Veterinary Laboratory, Weybridge, Surrey, United Kingdom. Recent field isolates of *Citrobacter diversus, Escherichia coli, Escherichia hermannii, Proteus vulgaris* and *Yersinia ruggerii* were also examined. All bacterial strains were stored on Dorset egg slopes and grown in peptone water for 18hours at 37° C.

Purification of SEFA:

Fimbrial antigens were prepared from *S. enteritidis* 468/86 which has been identified as expressing large quantities of the fimbriae.

The organisms were grown on Sensitest agar (Oxoid, Basingstoke, United Kingdom) overnight at 37° C. Bacteria were sedimented and suspended in phosphate buffered saline (PBS) pH 6.8. The fimbriae were then removed from the surface of the bacteria by heating the suspension at 60° C. for 30 min. The cell-free supernatant (crude SEFA) was first purified by DEAE-sepharose anion exchange chromatography (semi-pure SEFA) followed by size exclusion high-pressure liquid chromatography (pure SEFA). The purity of the SEFA preparations was determined by sodium dodecylsulphate-polyacrylamide gel-electrophoresis (SDS-PAGE) using 12.5% gels.

Rabbit antisera.

New Zealand White rabbits were injected subcutaneously into two separate sites with 50 micrograms of purified SEFA emulsified in Freunds Imcomplete Adjuvant (FIA). This was repeated seven and 21 days later and blood was collected 10 days after the final inoculation. The specificity of the antisera was checked by enzyme-linked immunosorbent assay (ELISA) and immune electron microscopy (IEM).

Production of MABs.

Female BALB/c mice were injected intraperitoneally with 50 micrograms of crude, semi-pure or pure SEFA as described in Table VI. Booster injections were carried out four and eight weeks after the first injection and spleens removed 3 days after the final one. Hybridomas were produced from fusion of murine splenocytes with the BALB/c myeloma cell line NS1 as described previously (5). Following cell fusion, hybridomas were distributed into 96-well microplates (NUNCLON, Roskilde, Denmark) and frequently tested for antibody production by ELISA as described below. Antibody-secreting hybridomas were expanded, cloned and stored. MABs from the resultant cloned cell lines together with MAB 69/25 were produced from murine ascitic fluid and concentrated tissue culture supernatant by standard techniques . The antibodies were partially purified by precipitation with ammonium sulphate (40% saturation) and dialysed against 0.01M PBS pH 7.2. The class and subclass of the antibodies was determined by immunodiffusion.

Direct-binding ELISAs.

The ELISAs used in this study were similar to those used for the production and binding of MAB 69/25 to the SEFA. The following direct-binding ELISAs were used:

(i) ELISA for screening hybridoma culture supernatants.

Wells of polystyrene microtitre plates were coated with 25 ng of pure SEFA diluted in 100 microliters of 0.1M phosphate buffer pH 4.5 by incubation overnight at 37° C. The plates were then washed and blocked before the addition of the culture supernatants. To detect MAB binding to the antigen, a peroxidase labelled anti-mouse immunoglobulin followed by the chromogenic substrate tetramethylbenzidine (Cambridge Veterinary Sciences, Ely, United Kingdom) were added and the enzyme reaction stopped with sulphuric acid and optical densities recorded at 450 nm.

(ii) ELISA for testing antibody specificity.

MABs from cloned hybridomas and rabbit antiserum against SEFA (RaSEFA) were tested by ELISA for binding to a variety of Salmonella and other bacteria. Organisms were grown in peptone water overnight, centrifuged at 3,000×g for 10 min. and suspended in PBS pH 7.2 to give a value of 1.25 at $A_{400}$. Antigens (100 microliters) prepared in this way were coated onto polystyrene microtitration plates in 0.1M carbonate buffer. pH 9.6 by incubation overnight at 37° C. Optimum concentrations of MABs were then examined for binding to the bacterial antigens using the procedures already described. Results were expressed as the percentage of MAB binding to the test strains relative to the binding in the high control in which normal mouse serum (Miles Laboratories, Slough, United Kingdom) was used in place of antigen. The binding of RaSEFA was detected by the addition of a biotinylated anti-rabbit immunoglobulin and biotinylated streptavidin-peroxidase complex (Amersham International, Amersham. United Kingdom).

Direct-blocking ELISA for epitope analysis.

MABs and RaSEFA were conjugated to horseradish peroxidase (Sigma Chemical Co., St. Louis. Mo.) by the method of Wilson and Nakane ((1978) In Knapp, Holubar and Wicks (ed.) Immunofluorescence and related staining techniques. Elsevier/North Holland Biomedical Press. Amsterdam). Wells of microtitre plates were coated with SEFA, blocked and washed as described above. The concentration of all MAbs was adjusted to twice the amount needed to saturate the antigen, and serial twofold dilutions of MAbs performed in PBS containing 0.05% (vol/vol) Tween 20 (PBST), incubated for 30 mins at 37° C. and the plates washed 6 times in PBST. Optimum dilutions of MAb or RaSEFA conjugates were then added (100 microliters) and incubated for 30 min at 37° C. and washed a further 6 times in PBST. Antibody binding was detected by the addition of TMB.

Immunoblot analysis.

Antigens containing SEFA were transferred from an SDS-PAGE gel to a nitrocellulose membrane and then reacted with the MABs.

Immune electron microscopy (IEM).

The binding of MABs and polyclonal RaSEFA to Salmonella strains was visualised by the addition of goldlabelled antiglobulins and viewed under the electron microscope.

Thiocyanate elution for measuring relative MAB affinity.

Elution of MABs from SEFA-coated microtitration wells by increasing concentrations of chaotropic thiocyanite ions (SCN), was determined as a measurement of relative affinity (see method of Macdonald et al, (1988) J. Immunol. Meth. 106: 191–194. MABs were added (100microliters) to SEFA-coated microtitre wells, incubated for 40 min at 37° C. and then washed 6 times in PBST. Various molarities of $NH_4SCN$ were added (100 microliters) to the wells and incubated for 15 min at room temperature and washed 6 times in PBST. The effect of $NH_4SCN$ on MAB binding was detected by the addition of goat anti-mouse immunoglobulin peroxidase conjugate for 30 min at 37° C. and TMB. The results are expressed as the lowest molarity of NH4 SCN causing 50% reduction in binding of MAB to SEFA.

MABs.

27 cloned hybridomas from four separate fusions secreted MAbs that bound to purified SEFA. 13 MAbs were selected for further study and Table VI gives details of their characteristics and the immunising antigen used for the production of the hybridomas. MAB 69/25 (SEFA-1) is included. The relative affinities of the MABs varied considerably as indicated by the range of thiocyanate molarities capable of eluting the MAB from SEFA (<1M to 5M SCN-). In general, however, MABs with similar affinities originated from the same fusion. The specificity of all the MABs except M73-11 and M73-12 was confirmed by reacting with the 14,300 SEFA in Western blots.

Direct-binding ELISAs.

The binding of MABs to Salmonella strains was measured. The 13 MABs bound strongly to all the strains of *S. enteritidis* and the single *S. moscow* examined. Five out of seven *S. dublin* strains exhibited weak MAB binding with all the MABs, whereas two strains of *S. dublin* failed to react with any of the MABs used in this study. The MABs did not bind to any other Salmonella serotypes or strains of bacteria from closely related genera. Polyclonal RaSEFA reacted identically to the MABs in the direct-binding ELISA.

Direct-blocking ELISA.

Each MAB was tested for its ability to block in serial twofold dilutions, the binding of peroxidase-conjugated MABs to epitopes on the SEFA. The results are expressed as the logarithm of the reciprocal of the highest dilution showing 50% blocking of the reaction compared with conjugated MAB alone. MABs which showed reciprocal blocking were regarded as binding to identical or overlapping epitopes, while MABs that did not block one another were assumed to identify different nonoverlapping epitopes.

Using the above criteria on 13 different MABs it is concluded that they represent 3 distinct epitope groups or clusters. Single MABs identifying the three epitope clusters partially blocked the binding of polyclonal RaSEFA to the antigen ($\leq 45\%$). When the MAb representing cluster 3 was combined with MAbs from cluster 1 or cluster 2 there was increased blocking of RaSEFA (45–55%). MABs from the three cluster groups blocked the RaSEFA by 70%.

IEM studies.

Specific immuno-gold labelling of SEFA occurred with all the MABs (Table VII) and RaSEFA. No difference in intensity or distribution of gold particles labelling SEFA was apparent when MABs from different epitope cluster groups were tested; the gold was distributed evenly throughout SEFA in all cases and was similar to the labelling of the fimbrial antigen with RaSEFA.

Individual MABs and RaSEFA reacted identically suggesting that SEFA consists of a number of highly conserved epitopes. Coupled with the results From our previous study, the results of the direct-binding ELISAs indicate that SEFA is expressed by only a few Salmanella serotypes all within serogroup D. All *S. enteritidis* strains grown in peptone water express large quantities of SEFA. However, under the same growth conditions most *S. dublin* strains express smaller quantities and some may not express SEFA at all.

Blocking ELISAs using MABs suggest that SEFA contains at least three epitope clusters. These may comprise of individual or groups of overlapping epitopes; the large size of MABs compared with individual epitopes precludes further interpretation. Furthermore, combinations of MABs from the three epitope clusters blocked the RaSEFA more effectively than MABs alone further suggesting the existence of more than one cluster. IEM studies revealed that the epitope clusters were distributed evenly along SEFA with no obvious difference in the number of repeats. Labelling with polyclonal RaSEFA produced similar numbers of gold particles associated with SEFA suggesting that the size of the rabbit antibodies and gold particles inhibits the binding to closely oriented epitopes. The fact that the majority of MABs reacted in Western blots indicate that the SEFA subunits contain a number of linear or continuous epitopes.

The two MABs which failed to react with SEFA in Western blots were able to reciprocally block MABs directed against continuous epitopes suggesting they too identify them. These two MABs had the lowest affinity towards SEFA which may account for their lack of reactivity in Western blots.

TABLE VI

Properties of 13 MABs specific to the SEFA.

| Immunising Antigens | MABs | Isotype | Immunoblot of the 14300 molecular wt. SEFA | IEM[a] | Relative[b] Affinity | Epitope Cluster |
|---|---|---|---|---|---|---|
| Whole *S. enteritidis* | SEFA-1 | IgG$_1$ | + | + | ++ | 1 |
| strain | SEFA-2 | IgG$_1$ | + | + | ++ | 1 |
| 1246/89 cells | SEFA-3 | IgG$_1$ | + | + | ++ | 1 |
| Crude and | SEFA-4 | IgA | + | + | ++++ | 3 |
| Semi-pure | SEFA-5 | IgA | + | + | ++++ | 3 |
| SEFA | SEFA-6 | IgA | + | + | ++++ | 3 |
| Semi-pure | SEFA-7 | IgG$_3$ | + | + | ++ | 2 |
| and pure | SEFA-8 | IgG$_3$ | + | + | ++ | 2 |
| SEFA | SEFA-9 | IgA | + | + | +++ | 2 |
|  | SEFA-10 | IgA | + | + | +++ | 2 |
|  | SEFA-11 | IgA | + | + | +++ | 2 |
| Semi-pure | SEFA-12 | IgM | − | ? | + | 1 |
| SEFA | SEFA-13 | IgM | − | ? | + | 1 |

[a]For details see text.
[b]Elution of MABs from SEFA with ≦ 1M ammonium thiocyanate
NH$_4$SCN = +; 1M NH$_4$SCN = ++; 2M NH$_4$SCN = +++; ≦ 3M NH$_4$SCN = ++++
SEFA-1 is MAB 69/25
SEFA-9 is MAB 71/3

ELECTRON MICROSCOPY FIGURES

Figure 1B:

FIGS. 1A and 1B are *S. enteritidis* negatively stained with PTA showing three distinct surface organelles. 1A; fine fimbrial material radiating from cell surface and a detached flagellum (arrow). Bar, 200 nm. 1B; fimbrial material (fa) forming matted appearance, and type 1 fimbriae (arrows). Bar 200 nm.

Figure 2A:
Figure 2B:

FIGS. 2A and 2B are *S. enteritidis* organisms probed with Mab 69/25 and labelled with immunogold. 1A; specific labelling of matted fimbrial antigen (fa) uniformly covering the cell surface. Bar, 600 nm. 2B; gold particles attached to matted fimbrial antigen (fa), but flagella and type 1 fimbriae (arrows) are unlabelled. Bar, 400 nm.

Figure 3:

FIG. 3 is two *S. dublin* organisms from culture probed with Mab 69/25 and labelled with immunogold. Cell 'a' is heavily labelled with gold particles. Cell 'b' does not exhibit surface fimbrial material and is unlabelled. Flagella fragments are unlabelled. Bar, 600 nm.

I claim:

1. A method of testing a sample for the presence of microorganisms for Salmonella serotypes expressing *Salmonella enteritidis* fimbrial antigen (SEFA) comprising the steps of:
   (a) exposing a sample suspected of containing the microorganisms, or SEFA to an antibody which specifically binds to the antigen specifically bound by the monoclonal antibody secreted by ECACC 90101101 or ECACC 90121902 or an antibody which specifically binds the epitope bound by the monoclonal antibody secreted by ECACC 90101101 or ECACC 90121902;
   (b) detecting antibody-antigen specific binding, wherein antigen-antibody specific binding is indicative of the presence of microorganisms selected from the group consisting of *S. enteritidis, S. dublin, S. moscow* and *S. blegdam*, and the absence of antibody-antigen specific binding is indicative of the absence of *S. enteritidis*.

2. A method of testing for the presence of a previous or current infection with Salmonella serotypes expressing SEFA comprising the steps of:
   (a) exposing said SEFA to a biological specimen obtained from a subject suspected of having a current or a previous Salmonella infection, wherein said SEFA specifically binds an antibody which specifically binds to the antigen specifically bound by the monoclonal antibody secreted by ECACC 90101101 or ECACC 90121902 or an antibody which specifically binds the epitope bound by the monoclonal antibody secreted by ECACC 90101101 or ECACC 90121902; then
   (b) detecting antibody-antigen specific binding wherein the presence of antibody-antigen specific binding is indicative of the presence of a previous or current Salmonella infection with microorganisms selected from the group consisting of *S. enteritidis, S. dublin, S. moscow* and *S. blegdam*, and the absence of antibody-antigen specific binding is indicative of the absence of a previous or current infection with *S. enteritidis*.

3. A method of determining whether a Salmonella serotype belongs to either a group consisting of *S. enteritidis, S. moscow and S. blegdam* or a group consisting of *S. dublin, S. moscow* and *S. blegdam* comprising the steps of:
   (a) exposing a sample suspected of containing at least one of said Salmonella serotypes to an antibody which specifically binds to the antigen specifically bound by the monoclonal antibody secreted by ECACC 90101101 or ECACC 90121902 or an antibody which specifically binds the epitope bound by the monoclonal antibody secreted by ECACC 90101101 or ECACC 90121902 and then detecting antibody-antigen binding, wherein antibody-antigen specific binding is indicative of the presence of a Salmonella serotype of either one of the groups; and
   (b) exposing a further sample of said sample suspected of containing at least one of said Salmonella serotypes to an antibody which specifically binds *S. enteritidis* but not *S. dublin* and detecting antibody-antigen specific binding wherein antibody antigen specific binding indicates the presence of *S. enteritidis, S. moscow* or *S. blegdam*.

4. A method as claimed in claim 1 further comprising step (c) exposing a further sample of said sample suspected of containing at least one of said Salmonella serotypes to an antibody which specifically binds *S. dublin* but not *S. enteritidis* and detecting antibody-antigen specific binding wherein antibody antigen specific binding indicates the presence of *S. dublin, S. moscow* or *S. blegdam*.

5. A method of testing a sample for the presence of organisms of the group of Salmonella serotypes expressing SEFA comprising the steps of:
   (a) seeding said sample suspected of containing the organisms into or onto a culture medium supporting the expression of Salmonella enteritidis fimbrial antigen;
   (b) culturing said sample in or on the culture medium; and
   (c) exposing a second sample obtained from the culturing step (b) to an antibody which specifically binds to the antigen specifically bound by the monoclonal antibody secreted by ECACC 90101101 or ECACC 90121902 or an antibody which specifically binds the epitope bound by the monoclonal antibody secreted by ECACC 90101101 or ECACC 90121902 and then detecting antibody-antigen specific binding wherein antibody-antigen specific binding is indicative of the presence of organisms of the group of Salmonella serotypes expressing SEFA.

6. A method a claimed in claim 5 wherein the culture medium is selected by screening candidate culture media for the ability to support the expression of SEFA by *S. enteritidis* or a SEFA-expressing strain of *S. dublin*, wherein the screening comprises culturing a sample of *S. enteritidis* or a SEFA-expressing strain of *S. dublin* in or on the candidate culture medium and exposing a second sample obtained from the culturing step to an antibody which specifically binds to the antigen specifically bound by the monoclonal antibody secreted by ECACC 90101101 or ECACC 90121902 or an antibody which specifically binds the epitope bound by the monoclonal antibody secreted by ECACC 90101101 or ECACC 90121902 and then detecting antibody-antigen specific binding wherein antibody-antigen specific binding is indicative of culture medium having the ability to support the expression of SEFA.

7. A method as claimed in claim 5 wherein the antibody is a monoclonal antibody expressed by one of the hybridoma cells deposited with the European Collection of Animal Cell Cultures (ECACC) under accession number 90101101 or 90121902.

8. A method as claimed in 5 wherein culturing in step (b) is carried out at a temperature of at least 22° C. such that SEFA produced uniformly covers the Salmonella cell.

9. A method as claimed in claim 5 wherein the culturing is carried out at a temperature of about 37° C.

10. A method as claimed in claim 5 wherein the culture medium is selected from the group consisting of Enriched E broth, Heart Infusion broth, peptone water pH 7.2, peptone water pH 6.0, Slanetz broth, desoxycholate citrate agar, MyConkey agar, nutrient agar, Salmonella Shigella agar, Sheep blood agar and xylose lysine descholate.

11. A method as claimed in claim 5 wherein the culture consists of 10–30 g/L Tyrptose™, 0.5 to 2.0 g/l glucose and 0.2 to 20 g/l agar.

12. A method as claimed in claim 5 wherein the culture medium consists of Enriched E broth, peptone water pH 7.2 or peptone water pH 6.0.

13. A method as claimed in claim 5 wherein the culture medium is selected from the group consisting of Sensitest agar and Isosensitest agar.

14. Hybridoma cells deposited at the European Collection of Animal Cell Cultures under accession numbers 90101101 or 90121902.

15. Monoclonal antibodies produced by the hybridoma cells deposited at the ECACC under accession numbers 90101101 or 90121902.

16. A test kit for testing a sample for the presence of microorganisms of Salmonella serotypes expressing SEFA comprising:

(a) hybridoma cells which produce antibodies which specifically bind the antigen specifically bound by the monoclonal antibody secreted by ECACC 90101101 or ECACC 90121902 or an antibody which specifically binds the epitope bound by the monoclonal antibody secreted by ECACC 90101101 or ECACC 90121902, or (b) monoclonal or polyclonal antibodies which specifically bind the antigen specifically bound by the monoclonal antibody secreted by ECACC 90101101 or ECACC 90121902 or an antibody which specifically binds the epitope bound by the monoclonal antibody secreted by ECACC 90101101 or ECACC 90121902, or (c) both (a) and (b).

17. A test kit as claimed in claim 16 wherein the hybridoma cells are deposited at the ECACC under accession numbers 90101101 or 90121902.

18. A test kit as claimed in claim 16 wherein the antibodies are monoclonal produced by the hybridoma cells deposited at the ECACC under accession numbers 90101101 or 90121902.

19. A test kit as claimed in claim 16 wherein the antibodies are immobilized on a solid carrier.

20. A test kit as claimed in claim 16 further comprising an antibody labelling agent for attaching a detectable label to the antibody.

21. A test kit as claimed in claim 20 wherein the detectable label comprises latex particles.

22. A test kit as claimed in claim 16 wherein the antibodies are conjugated to a detectable label.

23. A test kit as claimed in claim 16 further comprising components for preparation of a culture medium which causes or supports expression of SEFA by *S. enteritidis* or *S. dublin*.

24. A test kit as claimed in claim 23 wherein the components comprise the dry components for preparation of peptone water pH 7.2, peptone water pH 6.0, Sensitest agar or Isosensitest agar.

25. A test kit for use in a method of testing for the presence of a previous or current infection with Salmonella serotypes expressing SEFA, said test kit comprising SEFA, wherein the SEFA specifically binds an antibody which specifically binds to the antigen specifically bound by the monoclonal antibody secreted by ECACC 90101101 or ECACC 90121902 or an antibody which specifically binds the epitope bound by the monoclonal antibody secreted by ECACC 90101101 or ECACC 90121902.

26. A test kit as claimed in claim 25 wherein the SEFA is obtained form *S. enteritidis* or *S. dublin* microorganisms.

27. A test kit as claimed in claim 25 or claim 26 wherein the SEFA is in the form of detached fimbriae.

28. A test kit as claimed in claim 25 or 26 wherein the SEFA is immobilized on a solid substrate.

29. A test kit as claimed in claim 28 wherein the substrate is a microtiter plate.

30. An isolated polypeptide comprising SEFA which is specifically bound by an antibody which specifically binds to the antigen specifically bound by the monoclonal antibody secreted by ECACC 90101101 or ECACC 90121902 or an antibody which specifically binds the epitope bound by the monoclonal antibody secreted by ECACC 90101101 or ECACC 90121902.

31. An isolated polypeptide as claimed in claim 30 consisting of SEFA.

* * * * *